United States Patent [19]

Buckley

[11] Patent Number: 5,798,218
[45] Date of Patent: Aug. 25, 1998

[54] COMPOSITIONS AND METHODS FOR THE SPECIFIC DETECTION OF THY-1 ANTIGEN

[75] Inventor: James Thomas Buckley, Victoria, Canada

[73] Assignee: University of British Columbia Innovation and Development Corporation, Victoria, Canada

[21] Appl. No.: 724,298

[22] Filed: Sep. 24, 1996

[51] Int. Cl.$^6$ .................. G01N 33/50; G01N 33/543; C07K 14/195

[52] U.S. Cl. .................. 435/7.24; 435/7.7; 435/7.9; 435/325; 435/372.3; 435/4; 530/350

[58] Field of Search .................. 435/7.24, 4, 7.7, 435/7.9, 325, 372.3; 530/350

[56] References Cited

U.S. PATENT DOCUMENTS

| | | |
|---|---|---|
| 3,654,090 | 4/1972 | Schuurs and Van Weemen . |
| 3,992,631 | 11/1976 | Harte . |
| 4,171,311 | 10/1979 | Araps . |
| 4,201,763 | 5/1980 | Monthony et al. . |
| 4,517,303 | 5/1985 | Freytag et al. . |
| 5,480,799 | 1/1996 | O'Rand et al. . |
| 5,482,839 | 1/1996 | Ashihara et al. . |
| 5,541,103 | 7/1996 | Kanz et al. . |
| 5,556,598 | 9/1996 | Raybuck et al. . |

OTHER PUBLICATIONS

Pearson, et al., "The use of aerolysin toxin as an aid for visualization of low numbers of African trypanosomes in whole blood." *Acta Tropica* 39:73–77 (1982).

Howard, et al., "Nucleotide Sequence of the Gene for the Hold–Forming Toxin Aerolysin of Aeromonas hydrophila." *Journal of Bacteriology* 169:2869–2871 (1987).

Robert Hyman, "Somatic genetc analysis of the expression of cell surface molecules, " *TIG* 4:5–8 (1988).

Lemansky, et al., "Dynamics and Longevity of the Glycolipid–anchored Membrane Protein, Thy–1. " *The Journal of Cell Biology* 110:1525–1531 (1990).

Sugiyama, et al., "Identification of Defects in Glycosylphosphatidylinositol Anchor Biosynthesis in the Thy–1 Expression Mutants, " *The Journal of Biological Chemistry* 266:12119–12122 (1991).

Gruber, et al., "Partial purification of the rat erythrocyte receptor for the channel–forming toxin aerolysin and reconsittution into planar lipid bilayers." *Molecular Microbiology* 14:1093–1101 (1994) .

Michael W. Parker, F. Gisou van der Goot and J. Thomas Buckley, "Aerolysin —the ins and outs of a model channel–forming toxin." *Molecular Microbiology* 19:205–212 (1996).

*Primary Examiner*—Christina Y. Chan
*Assistant Examiner*—F. Pierre Vandervegt
*Attorney, Agent, or Firm*—Klarquist Sparkman Campbell Leigh & Whinston, LLP

[57] ABSTRACT

Aerolysin is shown to bind specifically to the Thy-1 antigen. Aerolysin-based methods, compositions and kits for detecting the presence of Thy-1 antigen are presented.

12 Claims, 10 Drawing Sheets

FIG. 1A

```
CGCCCCGAGT CAGCTGCGGC CGTTCACTCG CGACGGGCAC AGGCCCCTTG CTTGCGGTGG    60
CCGGTCACTC GCTGCAATTG CAGGGGTTGG GCACAATCAC CTTCGATGCC GGCACCCGCT   120
GGCTCAACGG CGGTCCCGCC GATCTGCAAC CGGTCGCCA  ACTGGTGCTG AGCCGCGATG   180
AAACGGGTCG GGCAACCGAG ATCCTGATCC CCAACCCCGA GGATGAACCG GAATAAGGAT   240
CATGCAGCCA AACGCTTAAT ATTTATTTTG CTAAATTAGA AATTTCTTTT TTATCTATAT   300
TCCAAAAGAT GATTAAGTGA CGAATAAAAT AATAGAGCGA GTGCTCTGAT ATTATATCAA   360
TCAATATTGA ATGAAGTTCA ATTTATGATT TTGTTAATAT ATTGCGCATA TTAAAAATGTG   420
GGCTGGATCG CATATTGAGA TTAATCTCAC TGATATTGTC GTACTCACAT GCCACCCGCT   480
GATATATAAG GTTGGTGAAT GCATGTCAAT GTTCAATATA TGGGGTTGC T ATG CAA     537
                                                     met gln
                                                     -23

AAA ATA AAA CTA ACT GGC TTG TCA TTA ATC ATA TCC GGC CTG CTG ATG    585
lys ile lys leu thr gly leu ser leu ile ile ser gly leu leu met
-20                                              -10

GCA CAG GCG CAA GCG GCA GAG CCC GTC TAT CCA GAC CAG CTT CGC TTG    633
ala gln ala gln ala ala glu pro val tyr pro asp gln leu arg leu
                    ▲1                                         10

TTT TCA TTG GGC CAA GGG GTC TGT GGC GTC GAC AAG TAT CGC CCC GTC AAT  681
phe ser leu gly gln gly val cys gly val asp lys tyr arg pro val asn
                                    20

CGA GAA GCC CAA AGC GTT AAA AGC AAT ATT GTC GGC ATG ATG GGG         729
arg glu ala gln ser val lys ser asn ile val gly met met gly
30                                                  40

CAA TGG CAA ATA AGC GGG CTG GCC AAC GGC TGG GTC ATT ATG GGG CCG    777
gln trp gln ile ser gly leu ala asn gly trp val ile met gly pro
```

FIG. 1B

```
                                                                            50
GGT TAT AAC GGT GAA ATA AAA CCA GGG ACA GCG TCC AAT ACC TGG TGT             825
gly tyr asn gly glu ile lys pro gly thr ala ser asn thr trp cys
 60                                          70

TAT CCG ACC AAT CCT GTT ACC GGT GAA ATA CCG ACA CTG TCT GCC CTG             873
tyr pro thr asn pro val thr gly glu ile pro thr leu ser ala leu
             80                                          90

GAT ATT CCA GAT GGT GAC GAA GTC GAT GTG CAG TGG CGA CTG GTA CAT             921
asp ile pro asp gly asp glu val asp val gln trp arg leu val his
                             100

GAC AGT GCG AAT TTC ATC AAA CCA ACC AGC TAT CTG GCC CAT TAC CTC             969
asp ser ala asn phe ile lys pro thr ser tyr leu ala his tyr leu
             110                                         120

GGT TAT GCC TGG GTG GGC GGC AAT CAC AGC CAA TAT GTC GGC GAA GAC            1017
gly tyr ala trp val gly gly asn his ser gln tyr val gly glu asp
                             130

ATG GAT GTG ACC CGT GAT GGC GAT GGC TGG GTG ATC CGT GGC AAC AAT            1065
met asp val thr arg asp gly asp gly trp val ile arg gly asn asn
             140                                         150

GAC GGC GGC TGT GAC GGC TAT CGC TGT GGT GAC AAG ACG GCC ATC AAG            1113
asp gly gly cys asp gly tyr arg cys gly asp lys thr ala ile lys
             160                                         170

GTC AGC AAC TTC GCC TAT AAC CTG GAT CCC GAC AGC TTC AAG CAT GGC            1161
```

FIG. 1C

```
val ser asn phe ala tyr asn leu asp pro asp ser phe lys his gly
                                    180

GAT GTC ACC CAG TCC GAC CGC CAG CTG GTC AAG ACT GTG GTG GGC TGG    1209
asp val thr gln ser asp arg gln leu val lys thr val val gly trp
         190                                        200

GCG GTC AAC GAC AGC GAC ACC CCC CAA TCC GGC TAT GAC GTC ACC CTG    1257
ala val asn asp ser asp thr pro gln ser gly tyr asp val thr leu
                            210

CGC TAC GAC ACA GCC ACC AAC TGG TCC AAG ACC AAC ACC TAT GGC CTG    1305
arg tyr asp thr ala thr asn trp ser lys thr asn thr tyr gly leu
         220                                    230

AGC GAG AAG GTG ACC ACC AAG AAC AAG TTC AAG TGG CCA CTG GTG GGG    1353
ser glu lys val thr thr lys asn lys phe lys trp pro leu val gly
                        240                                 250

GAA ACC CAA CTC TCC ATC GAG ATT CGT GCC AAT CAG TCC TGG GCG TCC    1401
glu thr gln leu ser ile glu ile arg ala asn gln ser trp ala ser
                                260

CAG AAC GGG GGC TCG ACC ACC ACC TCC CTG TCT CAG TCC GTG CGA CCG    1449
gln asn gly gly ser thr thr thr ser leu ser gln ser val arg pro
         270                                    280

ACT GTG CCG GCC CGC TCC AAG ATC CCG GTG AAG ATA GAG CTC TAC AAG    1497
thr val pro ala arg ser lys ile pro val lys ile glu leu tyr lys
                        290
```

FIG. 1D

```
GCC GAC ATC TCC TAT CCC TAT GAG TTC AAG GCC GAT GTC AGC TAT GAC   1545
ala asp ile ser tyr pro tyr glu phe lys ala asp val ser tyr asp
300                               310

CTG ACC AGC GGC TTC CTG CGC GGC GGC AAC GCC TGG TAT ACC            1593
leu thr ser gly phe leu arg gly gly asn ala trp tyr thr
        320                                       330

CAC CCG GAC AAC CGT CCG AAC TGG ACC ACC TTC GTC ATA GGT CCG       1641
his pro asp asn arg pro asn trp thr thr phe val ile gly pro
                340

TAC AAG GAC AAG GCG AGC AGC ATT CGG TAC CAG TGG GAC AAG CGT TAC   1689
tyr lys asp lys ala ser ser ile arg tyr gln trp asp lys arg tyr
350                               360

ATC CCG GGT GAA GTG AAG TGG TGG GAC TGG ACC ATA CAG CAG           1737
ile pro gly glu val lys trp trp asp trp thr ile gln gln
              370

AAC GGT CTG TCT ACC ATG CAG AAC CTG GCC AGA GTG CTG CGC CCG       1785
asn gly leu ser thr met gln asn leu ala arg val leu arg pro
        380                                       390

GTG CGG GCG GGG ATC ACC GGT GAT TTC AGT GCC GAG AGC CAG TTT GCC   1833
val arg ala gly ile thr gly asp phe ser ala glu ser gln phe ala
                400                                       410

GGC AAC ATA GAG GGT GCT CCC GTG CCG CTC GCG GCT GAC AGC AAG       1881
gly asn ile glu gly ala pro val pro leu ala ala asp ser lys
              420
```

FIG. 1E

```
GTG CGT CGT GCT CGC AGT GTG GAC GGC GCT GGT CAA GGC CTG AGG CTG   1929
val arg arg ala arg ser val asp gly ala gly gln gly leu arg leu
              430                                        440   ▲

GAG ATC CCG CTC GAT CGC GAA GAG CTC TCC GGG CTT GGC TTC AAC AAG   1977
glu ile pro leu asp arg glu glu leu ser gly leu gly phe asn lys
                        450

TCA GCC TCA GCG TGA CCCCTGCTGC CAATCAATAA CGGCAGGCG TTGTAGTGAT    2032
ser ala ser ala
460

GGAACCGGGC CTCTGTGGCC CGGTTTTTGT TTGCACTGGT CGGGCTTGTT AAAGGCTTGT 2092
GCTTTCCATT TCCCCACTTA TACTGGCGCC ATCTTGTCGG AGTGCCAACC GTCGAACGAC 2152
GCGAGGCTGA GACCGTTAAT TCGGGATCCG TGCAACCTCA TCAGGCTAGC ACCTGCGAAG 2212
GGAAACAAGG GTAACTTGCG GGTTGCCGCG CCGGGGGAGG GACAAGCCTC TCCGCGTCAT 2272
CAAGAGGAGC CATTCCTCGA TGAGTCAGGG CGCACAAGAG GGACTCTGTC CCGTCCGGTC 2332
TGCCCAGGAG GGGC                                                  2346
```

COMPOSITIONS AND METHODS FOR THE SPECIFIC DETECTION OF THY-1 ANTIGEN

BACKGROUND AND SUMMARY OF INVENTION

Aerolysin is a channel-forming cytolytic protein produced by virulent Aeromonas species, such as the important pathogen *Aeromonas hydrophila*. Aerolysin is one of the best studied of all of the bacterial cytolytic toxins. It is known to be secreted as a 52 kDa precursor called proaerolysin that can be converted to the active form by proteolytic removal of a C-terminal peptide. Many eucaryotic proteases can activate proaerolysin, as can proteases secreted by *A. hydrophila* itself. Once bound to a susceptible cell, aerolysin is transformed into an insertion-competent state by oligomerization. The oligomers, which are hetameric, bridge the lipid bilayer, producing discrete 1 nm channels which result in cell lysis.

Certain eucaryotic cells, including T-lymphocytes, are sensitive to very low levels of aerolysin (less than $10^{-9}$M). These highly susceptible cell types are lysed at much lower aerolysin concentrations than other cells. It is shown herein that aerolysin binds specifically to the Thy-1 antigen present on the surface of susceptible cell types. That is, Thy-1 is a high affinity receptor for the aerolysin toxin, and the presence of this receptor on certain cell types accounts for their great susceptibility to the toxin.

Thy-1 is a major surface antigen of T-lymphocytes, neurons and fibroblasts and is found abundantly in the thymus and brain tissue. The Thy-1 antigen is one of the best studied glycolipid-anchored proteins. The Thy-1 gene has been cloned from a number of species and the structures of its polypeptide, glycans and the glycosylphosphatidylinositol anchor are known. Thy-1 is the smallest known member of the immunoglobulin superfamily; it migrates as several bands around 30 Kda on SDS-Page, and it is known to be N-glycosylated at three positions. The molecular weight of the completely deglycosylated form is approximately 13 Kda. Thy-1 has been implicated in a disparate number of cellular processes including responses to heavy metals, changes in voltage-activated calcium currents, long-term potentiation of a memory, and lymphokine production. There is also evidence that clustering of Thy-1 molecules on T-lymphocytes by some antibodies can cause T-cell mitogenesis and apoptosis. There is, accordingly, much interest in the study and characterization of Thy-1 function.

The present invention is based on the discovery that aerolysin binds selectively and with high affinity to the Thy-1 antigen. Aerolysin is shown to bind specifically both to purified Thy-1and to Thy-1 present on the surface of cells. Less that 1 ng of Thy-1can be detected in whole cell extracts by probing Western blots with the toxin. Mouse T-lymphocyte cell lines that cannot produce native Thy-1, or that have had Thy-1 removed by treatment with phosphatidylinositol-specific phospholipase C, are much less sensitive to aerolysin.

This Thy-1 binding activity enables the use of aerolysin to detect the presence of Thy-1 antigen in biological samples. For example, aerolysin can be used to detect Thy-1 on Western blots (there is apparently no commercially available anti-Thy-1 antibody capable of detecting Thy-1-on Western blots). To facilitate the detection of Thy-1-aerolysin complexes, aerolysin may be conjugated to a detection agent such as an enzyme, cofactor, chromophore, fluorophore or radioactive marker. For example, aerolysin may be conjugated to biotin or peroxidase enzyme, or may be iodinated with $I^{125}$. Aerolysin can also be conjugated to a solid substrate and used to purify Thy-1 antigen by affinity chromatography. One aspect of the present invention is a conjugate comprising purified aerolysin conjugated to such a detection agent. Another aspect of the invention is purified aerolysin conjugated to a solid substrate, such as a microtiter plate.

Since aerolysin is a channel-forming toxin and will lyse cells to which it can bind, it may additionally be used to deplete Thy-$1^{30}$ cells in a mixed population of Thy-$1^+$ and Thy-$1^-$ cells.

Mutant forms of aerolysin which retain the capacity to specifically bind Thy-1 but are altered in one or more other functional characteristics are also encompassed in this invention and may be used in the same applications as "wild-type" aerolysin. For example, this invention also provides mutant forms of aerolysin which bind to Thy-1 but which lack the toxic function of "wild-type" aerolysin. Such non-toxic forms of aerolysin may be conjugated with fluorescent labels for use in conjunction with cell-sorting equipment to separate cells expressing Thy-1("Thy-$1^+$ cells") from cells that lack the Thy-1 antigen ("Thy-$1^-$cells"). Fluorophore-labeled aerolysin may also be used in fluorescence microscopy to detect the presence of Thy-1 on cells.

In light of the discovery of this activity of aerolysin and the recognition of its many uses, the present invention encompasses such uses, as well as compositions formulated to include aerolysin for use in these methods.

For example, one aspect of the present invention is a method of specifically detecting a Thy-1 antigen in a biological sample, the method comprising incubating the biological sample with a purified preparation of aerolysin. If there is Thy-1 antigen present in the sample, the aerolysin will bind to it and form an aerolysin-Thy-1 complex, and this complex can then be detected. Applications of this method include Western blotting, cell sorting, affinity chromatography and fluorescence microscopy. Such methods are useful to detect both the presence of free Thy-1 antigen as well as Thy-1 antigen present on the surface of cells, and may also be used to quantify Thy-1.

This invention also encompassed diagnostic kits for detecting Thy-1 antigen.

BRIEF DESCRIPTION OF THE DRAWINGS

FIG. 1 (SEQ ID No:1) shows,the nucleotide sequence of the aerolysin gene from *Aeromonas hydrophila* and the amino acid sequence of the encoded protein. Proteolytic processing sites of preproaerolysin and proaerolysin are shown with arrows.

FIG. 2 shows a Western blot of proteins developed using proaerolysin. Lane 1, proteins from EL-4 cells; Lane 2, total proteins from EL-4 GPI-mutant cells; Lane 3, total proteins from BW5 cells; Lane 4, total proteins from BW5 GPI-mutant cells.

FIG. 3 shows a Western blot developed using proaerolysin and illustrating the effect of N-glycosidase treatment on the proaerolysin binding component of EL-4 cells. Lanes 1 and 2, control EL-4 cells; lane 3 EL-4 cells treated with N-glycosidase.

FIG. 4 shows a Western blot developed using proaerolysin. Lane 1, Thy-1 deficient AKR1 cell proteins; lane 2, AKR1 cell proteins; lane 3, molecular weight standards; lane 4, EL-4 cell proteins.

FIG. 5 shows a Western blot of purified Thy-1 antigen developed using proaerolysin. Lane 1, 30 ng antigen; lane 2, 3 ng antigen; lane 3, 300 pg antigen.

FIG. 6 shows a Western blot of whole brain homogenates from different species developed using proaerolysin. Lane 1, human; lane 2, mouse; lane 3, pig; lane 4, rabbit; lane 5, rat; lane 6, cow; lane 7, lamb.

DETAILED DESCRIPTION OF THE INVENTION

1. Materials and methods

Biochemical procedures described herein are performed using standard laboratory methods as described in *Molecular Cloning: A Laboratory Manual*, 2nd ed., vol. 1–3, ed. Sambrook et al., Cold Spring Harbor Laboratory Press, Cold Spring Harbor, N.Y., 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992) and Harlow and Lane, *Antibodies: A Laboratory Manual*, Cold Spring Harbor Laboratory, Cold Spring Harbor, N.Y., 1988 (hereinafter "Harlow and Lane, 1988), unless otherwise noted.

Proaerolysin and aerolysin can be prepared in quantities sufficient for the applications described below by the method presented in reference 13. For example, proaerolysin can be isolated from culture supernatants of *Aeromonas salmonicida* CB3 transformed with the aerolysin gene (aerA) of *Aeromonas hydrophila* as follows. First, the culture supernatants are concentrated fifty-fold by ultra filtration and then centrifuged for two hours at 100,000 ×g to remove particulate matter. (*A. salmonicida* CB3 is a protease-deficient strain which can produce higher yields of aerolysin. Although protease-deficient strains are preferred since they give a higher yield of aerolysin, other transformed strains of Aeromonas, as well as other host cells and non-transformed Aeromonas strains may also be used.) The supernatant is then exchanged into 20 mM phosphate buffer containing 0.3M NaCl, pH 6.0, by passing it down a Sephadex G25 column. The resulting mixture is then applied to a hydroxyapatite column equilibrated in the same buffer. Proaerolysin is eluted from the column with a linear gradient formed by the starting buffer and 0.2M phosphate containing 0.3M NaCl, pH 6.0. Peak fractions are combined and the protein is precipitated by adding ammonium sulfate to 60% of saturation at 0° C. Following centrifugation, the precipitate is dissolved in 20 mM HEPES, pH 7.4, and applied to a Pharmacia DEAE Sepharose C16B column. Finally purified proaerolysin is eluted with a linear gradient formed by the starting buffer and 20 mM HEPES, 0.4M NaCl.

If desired, aerolysin can be produced from the purified proaerolysin either by adding trypsin to 1 µg/ml and incubating at room temperature for 10 min, or by adding 0.5 units/ml of immobilized trypsin and incubating with end over end mixing for 15 min. at room temperature. Immobilized trypsin can be removed by brief centrifugation; soluble trypsin can be inhibited by adding soybean trypsin inhibitor to 10 μg/ml.

2. Definitions

Aerolysin. As used herein, the term "aerolysin" refers to a bacterial toxin produced by members of the Aeromonas family, the essential characteristic of which is, for the purposes of this invention, its ability to bind specifically to Thy-1 antigen. "Aerolysin" includes not only the native toxin produced by Aeromonas sp., but also forms of this toxin produced by expressing the cloned *Aeromonas aerolysin* gene in other cell types, as well as mutant forms of the toxin which retain the ability to bind specifically to the Thy-1 antigen. As shown below, both the precursor form of the toxin (referred to in the literature as "proaerolysin") and the activated form (referred to in the literature as "aerolysin") bind specifically to Thy-1 and are thus encompassed within this definition of "aerolysin."

The amino acid sequences of aerolysin produced by various members of the Aeromonas family are highly conserved. The nucleotide sequence of the aerolysin gene of *Aeromonas hydrophila* and the amino acid sequence of the encoded peptide as reported by Howard et al. (1987) (reference 1 in the attached reference list) are shown in FIG. 1 (SEQ. ID No:1). The nucleotide sequences of aerolysin genes from other members of the Aeromonas family and the corresponding amino acid sequences of the encoded proteins are presented in references 2–5. Since the genes encoding these aerolysin toxins have been cloned, the toxin may be purified from various host cells transformed with an isolated *Aeromonas aerolysin* gene as described above. In addition, various mutant forms of aerolysin can readily be produced using standard mutagenesis techniques. Thus, "aerolysin" as used herein includes all forms of the toxin, include mutant forms, which retain the ability to specifically bind to Thy-1.

Preferably, the aerolysin used in the present invention is in purified form. In this context, "purified aerolysin" refers to a preparation of aerolysin in which the aerolysin has been separated from substantially all of the cellular proteins (if produced by lysis of cells) or from substantially all proteins in the growth medium (if purified from growth medium following secretion by cells). Preferably, the aerolysin will represent no less than 70% of the protein content of the preparation. However, it will be appreciated that the aerolysin preparation may be constituted using a carrier protein, such as serum albumin, in which case aerolysin may represent less than 70% of the protein content of the preparation.

Thy-1. The terms "Thy-1" and "Thy-1 antigen" are used here, as in the scientific literature, to refer to members of the well-characterized family of glycolipid-anchored membrane proteins expressed predominantly in the thymus, brain and T-lymphocytes of a wide range of mammals. There are many publications describing the amino acid sequences of Thy-1 antigens from different species, as well as studies on the expression of Thy-1 in certain cells types, the nature of its membrane association, and mutant forms of Thy-1. References 6–9 exemplify such studies.

Specific binding. This work shows that aerolysin binds specifically to Thy-1. Such specific binding means that when aerolysin is combined with an antigen mixture including Thy-1 antigen, the aerolysin molecules will bind substantially only to the Thy-1 antigen. Experimentally, such specific binding can be assessed by Western blotting of antigen mixtures and developing the Western blot first using aerolysin and then with an anti-aerolysin antibody conjugated to a detection agent, or simply using aerolysin linked directly to a detection agent (e.g. biotin). Specific binding of the aerolysin to Thy-1 will be evidenced by the presence of a single band at the molecular weight position corresponding to Thy-1. One skilled in the art will appreciate that some background binding (i.e. binding to other antigens) will occur; this may be observable as faint additional bands or a general light background binding.

3. Thy-1 is the high affinity receptor for aerolysin

Various mouse tissues were homogenized and dissolved in sample buffer for SDS polyacrylamide gel electrophoresis (SDS page). Following electrophoresis, the gel was transferred to nitrocellulose membrane by western blotting and then incubated by 1 μg/ml proaerolysin for one hour. Excess proaerolysin was removed by washing and the membranes were then incubated with rabbit anti-aerolysin polyclonal antibody conjugated with horseradish peroxidase enzyme. Excess antibody was removed by washing and bound antibody was then detected using electrochemiluminesence. In other experiments, the anti-aerolysin antibody was conjugated with alkaline phosphotase. This experiment demonstrated that brain and thymus tissues showed one or more intense proaerolysin-binding bands in the region of 30 Kda.

Figure 2:
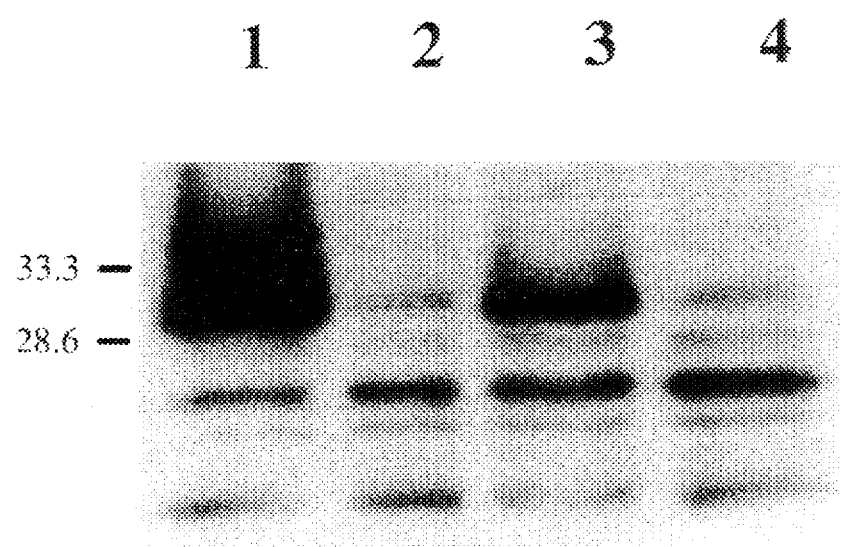

This same Western blotting technique was then used to determine the capacity of proaerolysin to bind to the mouse T-lymphocyte hybridoma cell lines EL-4 and BW5 and a similar binding pattern (i.e. in the region of 30 Kda.) was observed. However, binding of proaerolysin was noted to be significantly reduced in mutant forms of each of these cells lines that are unable to add glycosylphosphatidylinositol (GPI) anchors to cell surface proteins (see FIG. 2).

These results indicate that mouse brain and thymus contain a GPI-anchored protein that binds aerolysin. GPI-anchoring of the receptor on EL-4 cells was confirmed by treating the cells with a phosphatidylinositol (PI)-specific phospholipase C: reaction with the enzyme released a considerable fraction of the 30 Kda proaerolysin-binding protein, which could be recovered in soluble form in the culture supernatant.

Figure 3:
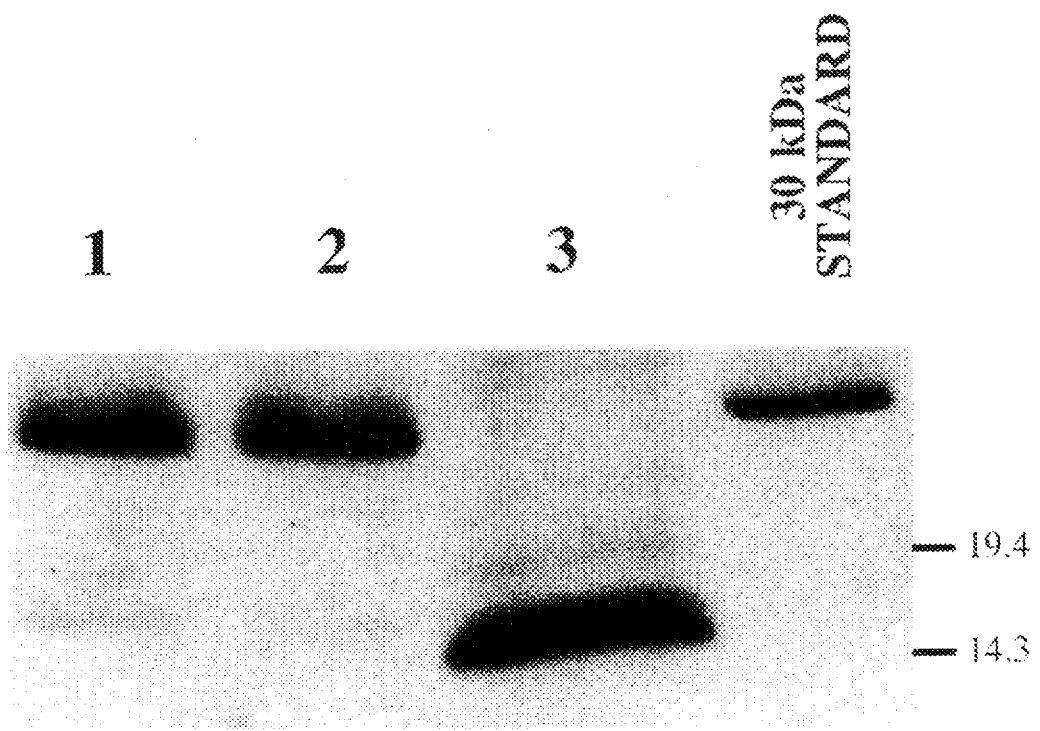

More than 100 different proteins are known to be attached to the plasma membrane by GPI-anchors, and several have been reported to be present on T-lymphocytes. One of these is Thy-1, a glycoprotein that migrates as two or more bands in the region of 30 Kda in SDS-PAGE gels. Thy-1 is the smallest known member of the immunoglobulin superfamily, and in mice and rats it is a major cell-surface component of thymocytes and brain. Thy-1 is knows to be N-glycosylated at 3 positions, and the molecular weight of the completely deglycosylated form is approx. 13 Kda. The results in FIG. 3 show that when EL-4 cell extracts are treated with N-glycosidase, the aerolysin binding component is reduced to a single band migrating in the area of 13 Kda. This result strongly suggested that the aerolysin receptor is Thy-1.

Figure 4:
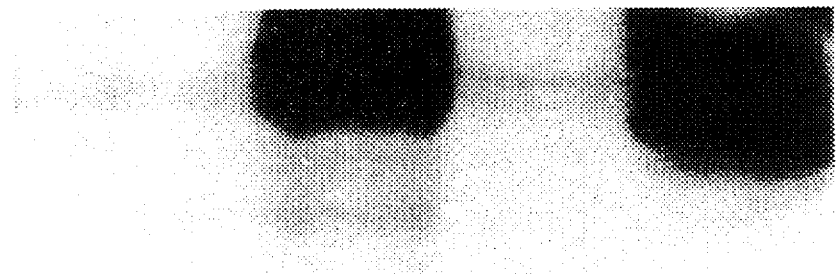

Confirmation that aerolysin binds Thy-1 was obtained from two additional experiments. In FIG. 4, a Western blot of an AKR1 T-cell lymphoma cell line probed with the protoxin is compared to a blot of a mutant AKR1 line that has a defective Thy-1 gene and cannot produce the protein (unlike the EL-4 and BW5 mutant cells that can express Thy-1 the protein). It is clear that the AKR mutant line contains little or no detectable proaerolysin binding bands corresponding to those observed above.

Figure 5:
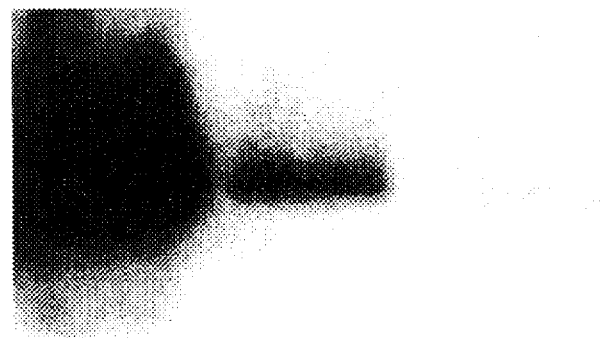

Final confirmation that aerolysin binds specifically to the Thy-1 antigen was obtained by performing Western blots on gels of varying amounts of purified rat thymus Thy-1. Development of these Western blots using proaerolysin (see FIG. 5) showed that proaerolysin is capable of detecting less than 500 pg of Thy-1 on such Western blots.

Figure 6:
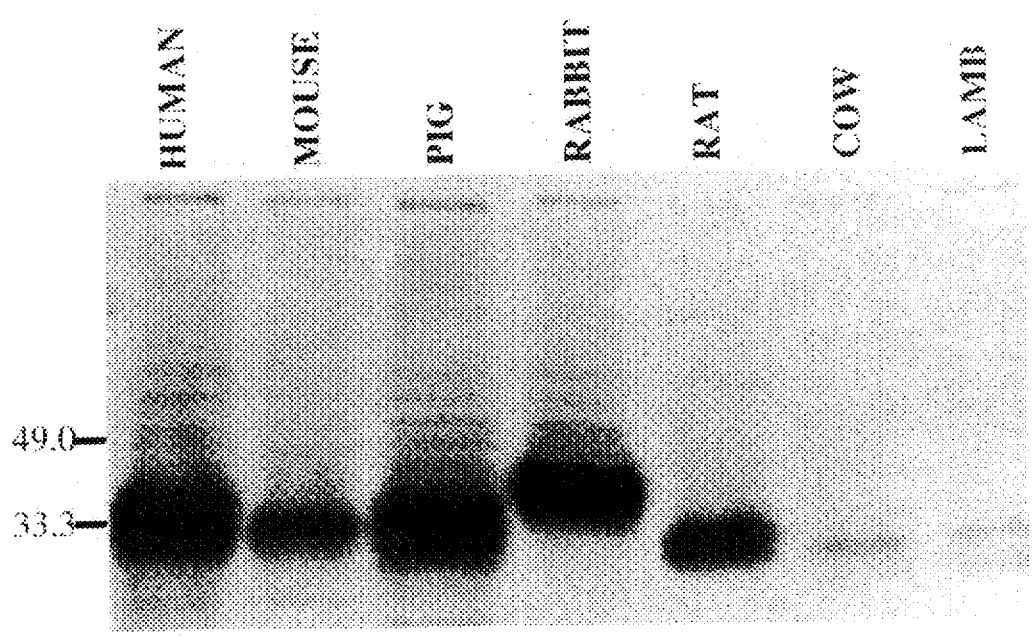

The results in FIG. 6 show that proaerolysin binding is not restricted to rat or mouse Thy-1. Rabbit, human and pig brain contain aerolysin-binding Thy-1 proteins of comparable size in similar amounts. Cow and sheep brain contained little or no proaerolysin-binding activity, however it was not determined whether this is because Thy-1 levels are low in brain tissue of these species (none of the commercially available anti-Thy-1 antibodies tested detect Thy-1 on Western blots), or whether it is because cow and sheet Thy-1 differ from the other species.

4. Sensitivity of Thy-1 bearing cells to aerolysin

A simple assay was employed to determine if EL-4 cells containing surface Thy-1 are more sensitive to aerolysin than cells that lack the receptor. Cells were incubated with 1 µM Po-Pro, a membrane impermeant probe which fluoresces when it intercalates with double stranded nucleic acid. The results indicated that when aerolysin is added to Thy-1$^+$cells, there is an increase in fluorescence after a delay that depends on the concentration of the toxin. Live/dead cell counts showed that all of the cells were dead by the time the fluorescence curve plateaus. Toxin concentrations at least as low as $10^{-9}$M resulted in 100% cell killing in 30 min. Pretreating the cells with phospholipase C (which releases Thy-1 from the cell surface) greatly reduced their sensitivity to the toxin in comparison to control cells. An El-4 mutant line that lacks the ability to add the complete GPI-anchor to Thy-1, and therefore cannot display the glycoprotein on the surface, was also much less sensitive to the toxin.

The data presented above show that aerolysin binds specifically to Thy-1. Illustrative applications and related aspects of this invention are set forth in the following examples.

EXAMPLE I

Preparation of aerolysin mutants

As discussed above, mutant forms of aerolysin may be prepared which retain the essential characteristic of being able to bind specifically to Thy-1. Such mutant forms may be produced by site-directed or other standard mutagenesis techniques, as described in Sambrook et al. (1989).

Because the nucleotide sequence of several aerolysin genes are known (see, for example, FIG. 1), one skilled in the art will readily be able to produce the gene using the polymerase chain reaction (PCR) procedure, as described by Innis et al. (1990) (reference 10). Methods and conditions for PCR amplification of DNA are described in reference 10 and Sambrook et al. (1989).

The selection of PCR primers for amplification of the aerolysin gene will be made according to the portions of the gene which are desired to be amplified. Primers may be chosen to amplify small fragments of the gene or the entire gene molecule. Variations in amplification conditions may be required to accommodate primers of differing lengths; such considerations are well known in the art and are discussed in reference 10. By way of example only, the entire aerolysin open reading frame may be amplified using the following primers.

Primer 1: 5' ATGCAAAAAATAAAACTAACTGGCTTG 3'(SEQ ID No.2)

Primer 2: 5' CGCTGAGGCTGACTTGAACGGAAGCCC 3'(SEQ ID No.3)

Template DNA for PCR amplification to produce the aerolysin gene can be extracted from Aeromonas sp. cells using standard techniques (see Sambrook et al., 1989).

The cloned aerolysin gene can readily be ligated into bacterial expression vectors for production of the encoded aerolysin. Standard methods and plasmid vectors for producing procaryotic proteins in E. coli are described in Sambrook et al. (1989). These methods facilitate large scale production of the protein and, if necessary, expression levels can be elevated by placing a strong, regulated promoter and an efficient ribosome binding site upstream of the cloned gene. Protease-deficient host cells are preferred since they yield higher levels of aerolysin.

The aerolysin gene may also be cloned into a suitable vector for mutagenesis. As noted, mutations in the sequence can readily be introduced using standard methods. Mutations in the aerolysin gene may result in deletions or additions to the encoded amino acid sequence, or may be substitutions of one amino acid for another. Amino-acid substitutions are preferably substitutions of single amino-acid residues. Substitutions may be "conservative," i.e. replacement of one amino acid with a different amino acid wherein the replacement has little or no effect on the structure or function of the polypeptide. A number of conservative amino acid substitutions are listed below in Table 1.

TABLE 1

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln |
| Met | leu; ile |
| Phe | met; leu; tyr |
| Ser | thr |
| Thr | ser |
| Trp | tyr |
| Tyr | trp; phe |
| Val | ile; leu |

Substantial changes in function of the polypeptide may be made by selecting substitutions that are less conservative than those listed above, e.g., causing changes in: (a) the structure of the polypeptide backbone in the area of the substitution; (b) the charge or hydrophobicity of the polypeptide at the target site; or (c) the bulk of an amino acid side chain. Substitutions generally expected to produce the greatest changes in protein properties are those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine. Mutant aerolysin s that have significant changes in their amino acid structure must still, for the purposes of this invention, be able to bind specifically to the Thy-1 antigen. A mutant not capable of specifically binding Thy-1 will fall outside of the definition of "aerolysin" as used herein. One of skill in the art will appreciate that the capability of a particular mutant peptide to bind Thy-1 may readily be ascertained using the Western blotting procedures described above. While many mutant forms of aerolysin that retain the essential characteristic of specific Thy-1 binding will be single amino acid substitutions, it will be appreciated that substantially shorter forms of aerolysin may also be produced which retain this ability. Such shorter forms would comprise, at a minimum, that portion of aerolysin capable of specifically binding to Thy-1.

Examples of mutant forms of the *Aeromonas hydrophila* aerolysin protein which differ in function from "wild-type" aerolysin are described in Table 2 below.

TABLE 2

| Mutation | Description of Mutation | Functional Characteristic of Mutant Form |
|---|---|---|
| H132N | His at position 132 changed to Asn | H132N cannot form oligomers. This mutant binds normally to Thy-1 but does not lyse cells. |
| W324A | Trp at position 324 changed to Ala | Mutant form cannot bind to rat or mouse Thy-1. |
| G202C | Gly at position 202 changed to Cys | Mutant can bind to Thy-1 but cannot insert into cell membrane. |
| T225G | Thr at position 225 changed to Gly | Mutant can bind Thy-1 but cannot insert into the membrane. |

Mutant forms of aerolysin which are capable of specifically binding to Thy-1 but which are nontoxic to cells may be used to label Thy-1$^+$ cells without affecting cell viability. H132N is an example of a non-toxic mutant aerolysin capable of binding specifically to Thy-1 antigen. Such mutants are useful in cell sorting experiments, separation of Thy-1$^{30}$ cells from a mixture and fluorescence microscopy.

If necessary, monoclonal antibodies may be produced to the aerolysin protein for use in the applications described below. Substantially pure aerolysin suitable for use as an immunogen is isolated from culture supernatants of transformed *Aeromonas salmonicida* or other host cells or native *Aeromonas* sp. cells, and the concentration of protein in the final preparation is adjusted, for example, by concentration on an Amicon filter device, to the level of a few milligrams per milliliter. Monoclonal antibody to the protein can then be prepared according to the classical method of Kohler and Milstein (1975) (reference 11) or derivative methods thereof. Briefly, a mouse is repetitively inoculated with a few micrograms of the selected purified protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described in reference 12, and derivative methods thereof. Selected positive clones can be expanded and their monoclonal antibody product harvested for use. Detailed procedures for monoclonal antibody production are described in Harlow and Lane (1988).

Optimally, monoclonal antibodies raised against aerolysin specifically detect aerolysin. That is, such antibodies recognize and bind aerolysin and do not substantially recognize or bind to other proteins found in bacterial or mammalian cells. Put another way, such antibodies have a specificity of binding to substantially only the aerolysin protein.

The determination that an antibody specifically detects aerolysin is made by any one of a number of standard immunoassay methods; for instance, the Western blotting technique (Sambrook et al., 1989). To determine that a given antibody preparation (such as one produced in a mouse) specifically detects aerolysin by Western blotting, total cellular protein is extracted from human cells, such as T-lymphocytes. As a positive control, total cellular protein is extracted from *Aeromonas* sp. cells. These protein preparations are then electrophoresed on a sodium dodecyl sulfate-polyacrylamide gel. Thereafter, the proteins are transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse Ig antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically detect aerolysin will, by this technique, be shown to bind to the aerolysin band in the Aeromonas cell extract lane (which will be localized at a given position on the gel determined by its molecular weight) but will not bind to the human cell extract lane. Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific aerolysin protein binding. Preferably, no antibody binding to the human cell extract would be observed. Anti-aerolysin monoclonal antibodies produced in this manner may be labeled with detection agents using standard techniques (see below).

EXAMPLE II

Use of aerolysin to detect Thy-1 antigen

The results presented above illustrate that aerolysin specifically binds to purified Thy-1 antigen as well as Thy-1 antigen present on the surface of cells. Accordingly, aerolysin may be used to detect and/or quantify the presence of Thy-1 antigen in a biological sample, as well as to separate Thy-1 antigen or Thy-1+ cells from antigen or cell mixtures. Such methods comprise the following core steps:

a. providing a biological sample to be tested;
b. providing a purified preparation of aerolysin;
c. combining the aerolysin with the biological sample; and then
d. detecting the presence of an aerolysin-Thy-1 antigen complex.

There are many applications of this core method. For example, one application is Western blotting (as described in Sambrook et al., 1989) wherein the biological sample is electrophoresed on an SDS-polyacrylamide gel and then transferred to a transfer membrane by the Western blotting procedure. Aerolysin is then used to bind to Thy-1 antigen fixed on the transfer membrane. Aerolysin-Thy-1 complexes can then be detected either directly if the aerolysin is conjugated to a detection agent such as biotin, or indirectly by use of anti-aerolysin antibodies conjugated with a detection agent. The use of aerolysin to detect Thy-1 in Western blotting is exemplified by the results shown above. This application may be particularly important to laboratory scientists since there is currently no commercially available method to detect Thy-1 on Western blots.

Another application is the detection of Thy-1 in a biological sample wherein the sample is contacted with a solid substrate to whichi aerolysin is attached. Complexes of Thy-1 and aerolysin will remain on the substrate after excess sample is washed off, and these complexes can then be detected. For example, the biological sample may be a serum sample from a patient. In particular embodiments of this application, the method may be used not only to detect the presence of Thy-1, but also to quantify the amount of the antigen present in the biological sample.

Another application of this core method is affinity purification of Thy-1 from a mixture of antigens. In such a method, aerolysin is incubated with the antigen mixture and then loaded onto an affinity column to which are attached antibodies specific for aerolysin. The Thy-1-aerolysin complexes bind to the antibodies in the column and can subsequently be released from the column for quantification. Suitable methods for disrupting Thy-1 aerolysin complexes include addition of glycine at extreme pH (e.g. pH 2 or pH 11) and other methods known in the art for disrupting protein complexes.

Alternatively, the antigen mixture may be directly applied to an affinity column to which aerolysin has been attached. Similarly, cells expressing Thy-1 may be separated from a mixture of cells using aerolysin columns. Preferably, the aerolysin used to separate such cells would be a mutant form of aerolysin capable of binding to Thy-1 but lacking the ability to lyse cells once it had bound. A suitable mutant would be the H132N mutant described above. U.S. Pat. No. 5,556,598 describes affinity purification procedures and presents a method of affinity purification using a pipette tip device including an internal membrane incorporating a binding agent. Such a device could be operated with aerolysin as the binding agent incorporated into the membrane for the purification of Thy-1 antigen or Thy-1 cells.

Other applications of this technology include the use of aerolysin conjugated to a fluorescent detection agent in fluorescence activated cells sorters (FACS, available, e.g. from Becton Dickinson) to enrich for Thy-1+ cells (see U.S. Pat. No. 5,541,103), and in fluorescence microscopy to detect Thy-1 antigen on the surface of cells. Again, mutant forms of aerolysin which do not lyse cells are preferred in such applications.

In each of this applications, it may be advantageous to label the aerolysin with a detection agent to facilitate detection of aerolysin-Thy-1 antigen complexes. Furthermore, for antigen or cell purification applications, it may be useful to attach to the aerolysin to a solid substrate.

1. Labeling of aerolysin with a detection agent

Methods of detecting Thy-1 antigen using aerolysin can take two different forms: direct and indirect detection methods. In indirect detection methods, aerolysin is incubated with a biological sample to allow for the formation of aerolysin-Thy-1 complexes, and these complexes are subsequently detected by a secondary reagent, such as labeled anti-aerolysin antibodies. Such antibodies are labeled with a particular detection agent which facilitates the subsequent detection of aerolysin-Thy-1 antibody complexes. In direct detection methods, the need for a secondary reagent (such as the antibody in the above example) is obviated by directly labeling the aerolysin with a detection agent.

Suitable detection agents are well known in the art and are commonly used in standard diagnostic applications. See, for example, U.S. Pat. Nos. 3,654,090, 4,201,763, 4,171,311, 3,992,631, 5,480,799 and 5,482,839. Detection agents suitable for labeling aerolysin include: radionuclides (such as $I^{125}$); enzymes (such as peroxidase, alkaline phosphatase and β-galactosidase); cofactors (such as biotin); fluorochromes (such as fluorescein, rhodamine, Texas red and phycoerythrin); chromophores; and magnetic particles. Aerolysin conjugated to fluorochrome detection agents are particularly useful in cell sorting using FACS cell sorters, and in fluorescence microscopy.

Conjugating aerolysin to one of these detection agents can be performed using standard techniques, similar to those for labeling antibodies with these detection agents. U.S. Pat. Nos. 3,654,090, 4,201,763, 4,171,311, 3,992,631, 5,480,799 and 5,482,839, and chapter 9 of Harlow and Lane (1988) describe protocols that may be used for conjugating detection agents to aerolysin.

For example, proaerolysin and aerolysin may be labeled with the fluorescent probe 5-((((2-iodoacetyl)amino)ethyl) amino)naphthalene-1-sulphonic acid (AEDANS). A number of mutant forms of aerolysin with single cysteine substitutions have been made including E29C, C159S, K171C, G202C and I445C. These mutants appear to bind normally to Thy-1 and the cysteines in these mutants can be labeled with biotin using N-[6-(biotinamide)hexyl]-3'-(2'-pyridylthio)propionamide, or with fluorescein using iodoacetamidofluorescein. The single cysteine mutant E407C does not appear to bind normally to Thy-1. Logically, detection agents should not be conjugated to residues which, as demonstrated by mutation studies, are critical for binding.

Step (d) in the core method described above—detecting the presence of an aerolysin-Thy-1 antigen complex—is dependent on whether the application is a direct method or an indirect detection method. In direct methods the aerolysin is conjugated to a detection agent and may be detected directly. In indirect methods, a labeled reagent, such as an anti-aerolysin monoclonal antibody labeled with a detection agent is employed, and the presence of this reagent bound to aerolysin is detected. In either case however, the final step will be a detection/quantification step, the nature of which will depend on the particular detection agent selected. Detection steps for the specific detection agents discussed above are well known in the art and are discussed in Sambrook et al (1989); Harlow and Lane (1988) and U.S. Pat. Nos. 5,482,839 and 5,480,799. For examples, where the specific detection agent is the enzyme β-galactosidase, the presence of enzyme may be detected using the substrate p-nitrophenyl-0-galactose; photographic film or a scintillation counter may be used to detect aerolysin labeled with a radionuclide; and an avidin-based substrate may be used to detect aerolysin labeled with biotin (for example, SIH™ kits marketed by Sigma Diagnostics, St. Louis, Mo. may be employed).

2. Attaching aerolysin to a solid substrate

Methods for attaching proteins to solid substrates are well-known in the art and are described, for example, in U.S. Pat. No. 5,480,799 and U.S. Pat. No. 5,482,839. Attachment of aerolysin to the solid substrate may be accomplished by physical adsorption or chemical bonding. Physical adsorption may be performed by reaction between the solid substrate and the purified aerolysin in a suitable buffer solution. Chemical bonding may be performed using standard methods for attaching peptides to solid surfaces such as the carbodiimide method, or the use of divalent cross linking agents such as glutaraldehyde.

Solid substrates to which aerolysin may be attached for use in affinity purification techniques include plastic petri dishes and test tubes, polystyrene beads, Sephadex beads, plastic cartridges and pipette tips (which may be made of inter alia polycarbonate, polypropylene or polystyrene resin), microtiter plates, magnetic particles, membranes, such as nitrocellulose, nylon and cellulose membranes, fiberglass, cellulose acetate and magnetic particles.

As described in U.S. Pat. No. 5,482,839, when the solid substrate is a magnetic particle, separation of the particles from the biological sample is achieved by applying an external magnetic field to the sample.

EXAMPLE III

Kits for detecting/quantifying/separating Thy-1 antigen and Thy-1$^+$ cells

One aspect of the present invention is the provision of a conjugate comprising purified aerolysin conjugated to a detection agent. In addition, a kit containing the required components for carrying out a diagnostic test for detecting the presence of Thy-1 antigen can be assembled. In one embodiment, such a kit comprises a package containing purified aerolysin conjugated with a detection agent, and may also include substrates suitable for quantification or detection of the aerolysin-detection agent conjugate.

In another embodiment, suitable for use in indirect detection methods, the kit comprises purified aerolysin and an anti-aerolysin antibody conjugated to a detection agent. Such a kit may also include substrates for detecting the presence of, or quantifying, the anti-aerolysin-detection agent conjugate.

In other embodiments of these kits, the aerolysin may be a mutant form of aerolysin which retains the ability to specifically bind to Thy-1 antigen but which lacks to the capacity to lyse cells to which it binds. Such kits are particularly useful for detecting, quantifying or selecting cells that express Thy-1.

In another embodiment, the aerolysin (whether or not conjugated to a detection agent) may be provided in the kit attached to a solid substrate, such as an affinity column or the wells of a microtiter plate.

EXAMPLE IV

Depletion of Thy-1$^+$ cells using aerolysin

As illustrated above, when aerolysin binds to a Thy-1$^+$ cell, cell lysis results. Thus, aerolysin may be used to selectively deplete Thy-1$^+$ cells from a mixed population of cells. Thus, a sufficient quantity of aerolysin may be added to a mixed population of B-lymphocytes and T-lymphocytes. Since only T-lymphocytes express the Thy-1 antigen, aerolysin will bind to these cells and not to the B-lymphocytes. Insertion of the aerolysin toxin into the membrane of the T-lymphocytes will follow binding of the toxin and will result in lysis of the T-lymphocytes. Accordingly, only B-lymphocytes will remain in the sample.

Having illustrated and described the principles of the present invention, it will be apparent to persons skilled in the art that the invention can be modified in arrangement and detail without departing from such principles. I claim all modifications that are within the spirit and scope of the appended claims.

All publications and published patent documents cited in this specification are incorporated herein by reference to the same extent as if each individual publication or patent application was specifically and individually indicated to be incorporated by reference.

REFERENCES

1. Howard et al. (1987), "Nucleotide Sequence of the Gene for the Hole-Forming Toxin Aerolysin of Aeromonas hydrophila," J. Bacteriol. 169, 2869–2871.
2. Hirono et al. (1992), "Nucleotide Sequences and Characterization of Haemolysin Genes from *Aeromonas hydrophila* and *Aeromonas sobria*," *Microb. Pathog.* 13, 433–446.
3. Hirono, I. and Aoki, T. (1993), "Cloning and Characterization of Three Hemolysin Genes from *Aeromonas salmonicida*," *Microb. Pathog.* 15, 269–282.
4. Husslein et al. (1988), "Nucleotide Sequence and Transcriptional Analysis of the aerCaer A Region of *Aeromonas sobria* encoding Aerolysin and its Regulatory Region," *Mol. Microbiol.* 2, 507–517.

5. Chopra et al. (1993). "Cloning, Expression, and Sequence Analysis of a Cytolytic Enterotoxin Gene from Aeronomas hydrophila," Can. J. Microbiol. 39, 513–523.
6. Seki et al. (1985). "The Human Thy-1 Gene: Structure and Chromosomal Location." Proc. Natl. Acad. Sci. U.S.A. 82, 6657–6661.
7. Hyman, R. (1988). "Somatic Genetic Analysis of the Expression of Cell Surface Molecules." Trans in Genetics 4, 5–8.
8. Lemansky et al. (1990). "Dynamics and Longevity of the Glycolipid-Anchored Membrane Protein, Thy-1." J. Cell Biol. 110, 1525–1531.
9. Sugiyama et al. (1991). "Identification of Defects in Glycosylphosphatidylinositol Anchor Biosynthesis in the Thy-1 Expression Mutants." J. Biol. Chem. 266, 12119–12122.
10. Innis et al. (Eds.) (1990). PCR Protocals, A Guide to Methods and Applications, Academic Press, Inc., San Diego, Calif.
11. Kohler and Milstein (1975). Nature 256:495.
12. Engvall (1980). Enzymol. 70:419.
13. Buckley J. T. and Howard S. P. (1988) Aerolysin from Aeromonas hydrophila. Methods Enzymol. (1988) 165: 193–9.

---

I claim:

1. A method of specifically detecting a Thy-1 antigen, comprising:
providing a biological sample to be tested;
providing a purified preparation of aerolysin;
combining the aerolysin with the biological sample; and
detecting the presence of an aerolysin-Thy-1 antigen complex.

2. The method of claim 1 wherein the Thy-1 antigen is associated with a membrane of a cell.

3. The method of claim 1 wherein the Thy-1 antigen is expressed on the surface of a lymphocyte.

4. The method of claim 1 wherein the aerolysin is conjugated with a detection agent.

5. The method of claim 4 wherein the detection agent is selected from the group consisting of enzymes, cofactors, chromophores, fluorophores, magnetic particles and radionuclides.

6. A method for detecting the presence of a Thy-1 antigen in a biological sample, comprising:
combining the biological sample with a sufficient quantity of a conjugate comprising a purified aerolysin molecule conjugated to a detection agent; and
detecting the presence of a conjugate-Thy-1 complex.

7. A method of removing cells bearing a Thy-1 antigen from a mixture of cells comprising the steps of:
contacting the mixture of cells with a composition comprising a purified aerolysin molecule conjugated to a solid substrate such that Thy-1 antigen binds to the aerolysin;
removing the mixture from the solid substrate.

8. A method of depleting a population of Thy-1$^+$ cells comprising incubating the cells with a sufficient quantity of aerolysin, wherein the aerolysin is capable of causing lysis of Thy-1$^+$ cells.

9. The method of claim 7 wherein said purified aerolysin molecule is a non-toxic mutant aerolysin selected from the group consisting of H132N, G202C and T225G.

10. The method of claim 1 wherein said purified preparation of aerolysin is a non-toxic mutant aerolysin selected from the group consisting of H132N, G202C and T225G.

11. The method of claim 6 wherein the detection agent is selected from the group consisting of enzymes, cofactors, chromophores, fluorophores, magnetic particles and radionuclides.

12. The method of claim 7 wherein the solid substrate is selected from the group consisting of microtiter plate wells, affinity columns, beads, petri dishes and membranes.

* * * * *

UNITED STATES PATENT AND TRADEMARK OFFICE
CERTIFICATE OF CORRECTION

PATENT NO. : 5,798,218
DATED : August 25, 1998
INVENTOR(S) : James Thomas Buckley It is certified that error appears in the above-identified patent and that said Letters Patent is hereby corrected as shown below: On the title page, item [73]

change Assignee "University of British Columbia" to --University of Victoria Innovation and Development Corporation--.

Signed and Sealed this

Twentieth Day of July, 1999

Attest:

Q. TODD DICKINSON

*Attesting Officer*          *Acting Commissioner of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 2346
        ( B ) TYPE: nucleic acid
        ( C ) STRANDEDNESS: double
        ( D ) TOPOLOGY: circular ( x i ) SEQUENCE DESCRIPTION: SEQ ID NO:1:

```
CGCCCCGAGT  CAGCTGCGGC  CGTTCACTCG  CGACGGGCAC  AGGCCCCTTG  CTTGCGGTGG        60

CCGGTCACTC  GCTGCAATTG  CAGGGGTTGG  GCACAATCAC  CTTCGATGCC  GGCACCCGCT       120

GGCTCAACGG  CGGTCCCGCC  GATCTGCAAC  CGGGTCGCCA  ACTGGTGCTG  AGCCGCGATG       180

AAACGGGTCG  GGCAACCGAG  ATCCTGATCC  CCAACCCCGA  GGATGAACCG  GAATAAGGAT       240

CATGCAGCCA  AACGCTTAAT  ATTTATTTTG  CTAAATTAGA  AATTTCTTTT  TTATCTATAT       300

TCCAAAAGAT  GATTAAGTGA  CGAATAAAAT  AATAGAGCGA  GTGCTCTGAT  ATTATATCAA       360

TCAATATTGA  ATGAAGTTCA  ATTTATGATT  TTGTTAATAT  ATTGCGCATA  TTAAAATGTG       420

GGCTGGATCG  CATATTGAGA  TTAATCTCAC  TGATATTGTC  GTACTCACAT  GCCACCCGCT       480

GATATATAAG  GTTGGTGAAT  GCATGTCAAT  GTTCAATATA  TTGGGGTTGC  T ATG CAA       537
                                                           met gln
                                                             1
```

```
AAA ATA AAA CTA ACT GGC TTG TCA TTA ATC ATA TCC GGC CTG CTG ATG            585
lys ile lys leu thr gly leu ser leu ile ile ser gly leu leu met
          5                   10                  15

GCA CAG GCG CAA GCG GCA GAG CCC GTC TAT CCA GAC CAG CTT CGC TTG            633
ala gln ala gln ala ala glu pro val tyr pro asp gln leu arg leu
        20                  25                  30

TTT TCA TTG GGC CAA GGG GTC TGT GGC GAC AAG TAT CGC CCC GTC AAT            681
phe ser leu gly gln gly val cys gly asp lys tyr arg pro val asn
 35                  40                  45                  50

CGA GAA GAA GCC CAA AGC GTT AAA AGC AAT ATT GTC GGC ATG ATG GGG            729
arg glu glu ala gln ser val lys ser asn ile val gly met met gly
                    55                  60                  65

CAA TGG CAA ATA AGC GGG CTG GCC AAC GGC TGG GTC ATT ATG GGG CCG            777
gln trp gln ile ser gly leu ala asn gly trp val ile met gly pro
                70                  75                  80

GGT TAT AAC GGT GAA ATA AAA CCA GGG ACA GCG TCC AAT ACC TGG TGT            825
gly tyr asn gly glu ile lys pro gly thr ala ser asn thr trp cys
         85                  90                  95
```

```
TAT CCG ACC AAT CCT GTT ACC GGT GAA ATA CCG ACA CTG TCT GCC CTG                873
tyr pro thr asn pro val thr gly glu ile pro thr leu ser ala leu
    100              105                 110

GAT ATT CCA GAT GGT GAC GAA GTC GAT GTG CAG TGG CGA CTG GTA CAT                921
asp ile pro asp gly asp glu val asp val gln trp arg leu val his
115              120                 125                         130

GAC AGT GCG AAT TTC ATC AAA CCA ACC AGC TAT CTG GCC CAT TAC CTC                969
asp ser ala asn phe ile lys pro thr ser tyr leu ala his tyr leu
                135                 140                 145

GGT TAT GCC TGG GTG GGC GGC AAT CAC AGC CAA TAT GTC GGC GAA GAC               1017
gly tyr ala trp val gly gly asn his ser gln tyr val gly glu asp
            150                 155                 160

ATG GAT GTG ACC CGT GAT GGC GAC GGC TGG GTG ATC CGT GGC AAC AAT               1065
met asp val thr arg asp gly asp gly trp val ile arg gly asn asn
        165                 170                 175

GAC GGC GGC TGT GAC GGC TAT CGC TGT GGT GAC AAG ACG GCC ATC AAG               1113
asp gly gly cys asp gly tyr arg cys gly asp lys thr ala ile lys
    180                 185                 190

GTC AGC AAC TTC GCC TAT AAC CTG GAT CCC GAC AGC TTC AAG CAT GGC               1161
val ser asn phe ala tyr asn leu asp pro asp ser phe lys his gly
195                 200                 205                 210

GAT GTC ACC CAG TCC GAC CGC CAG CTG GTC AAG ACT GTG GTG GGC TGG               1209
asp val thr gln ser asp arg gln leu val lys thr val val gly trp
                215                 220                 225

GCG GTC AAC GAC AGC GAC ACC CCC CAA TCC GGC TAT GAC GTC ACC CTG               1257
ala val asn asp ser asp thr pro gln ser gly tyr asp val thr leu
            230                 235                 240

CGC TAC GAC ACA GCC ACC AAC TGG TCC AAG ACC AAC ACC TAT GGC CTG               1305
arg tyr asp thr ala thr asn trp ser lys thr asn thr tyr gly leu
        245                 250                 255

AGC GAG AAG GTG ACC ACC AAG AAC AAG TTC AAG TGG CCA CTG GTG GGG               1353
ser glu lys val thr thr lys asn lys phe lys trp pro leu val gly
    260                 265                 270

GAA ACC CAA CTC TCC ATC GAG ATT GCT GCC AAT CAG TCC TGG GCG TCC               1401
glu thr gln leu ser ile glu ile ala ala asn gln ser trp ala ser
275                 280                 285                 290

CAG AAC GGG GGC TCG ACC ACC ACC TCC CTG TCT CAG TCC GTG CGA CCG               1449
gln asn gly gly ser thr thr thr ser leu ser gln ser val arg pro
                295                 300                 305

ACT GTG CCG GCC CGC TCC AAG ATC CCG GTG AAG ATA GAG CTC TAC AAG               1497
thr val pro ala arg ser lys ile pro val lys ile glu leu tyr lys
            310                 315                 320

GCC GAC ATC TCC TAT CCC TAT GAG TTC AAG GCC GAT GTC AGC TAT GAC               1545
ala asp ile ser tyr pro tyr glu phe lys ala asp val ser tyr asp
        325                 330                 335

CTG ACC CTG AGC GGC TTC CTG CGC TGG GGC GGC AAC GCC TGG TAT ACC               1593
leu thr leu ser gly phe leu arg trp gly gly asn ala trp tyr thr
    340                 345                 350

CAC CCG GAC AAC CGT CCG AAC TGG AAC CAC ACC TTC GTC ATA GGT CCG               1641
his pro asp asn arg pro asn trp asn his thr phe val ile gly pro
355                 360                 365                 370

TAC AAG GAC AAG GCG AGC AGC ATT CGG TAC CAG TGG GAC AAG CGT TAC               1689
tyr lys asp lys ala ser ser ile arg tyr gln trp asp lys arg tyr
                375                 380                 385

ATC CCG GGT GAA GTG AAG TGG TGG GAC TGG AAC TGG ACC ATA CAG CAG               1737
ile pro gly glu val lys trp trp asp trp asn trp thr ile gln gln
            390                 395                 400

AAC GGT CTG TCT ACC ATG CAG AAC AAC CTG GCC AGA GTG CTG CGC CCG               1785
asn gly leu ser thr met gln asn asn leu ala arg val leu arg pro
        405                 410                 415
```

-continued

| | | | | | | | | | | | | | | | | |
|---|---|---|---|---|---|---|---|---|---|---|---|---|---|---|---|---|
| GTG | CGG | GCG | GGG | ATC | ACC | GGT | GAT | TTC | AGT | GCC | GAG | AGC | CAG | TTT | GCC | 1833 |
| val | arg | ala | gly | ile | thr | gly | asp | phe | ser | ala | glu | ser | gln | phe | ala | |
| | 420 | | | | | 425 | | | | | 430 | | | | | |
| GGC | AAC | ATA | GAG | ATC | GGT | GCT | CCC | GTG | CCG | CTC | GCG | GCT | GAC | AGC | AAG | 1881 |
| gly | asn | ile | glu | ile | gly | ala | pro | val | pro | leu | ala | ala | asp | ser | lys | |
| 435 | | | | | 440 | | | | | 445 | | | | | 450 | |
| GTG | CGT | CGT | GCT | CGC | AGT | GTG | GAC | GGC | GCT | GGT | CAA | GGC | CTG | AGG | CTG | 1929 |
| val | arg | arg | ala | arg | ser | val | asp | gly | ala | gly | gln | gly | leu | arg | leu | |
| | | | | 455 | | | | | 460 | | | | | 465 | | |
| GAG | ATC | CCG | CTC | GAT | CGC | GAA | GAG | CTC | TCC | GGG | CTT | GGC | TTC | AAC | AAG | 1977 |
| glu | ile | pro | leu | asp | arg | glu | glu | leu | ser | gly | leu | gly | phe | asn | lys | |
| | | | 470 | | | | | 475 | | | | | 480 | | | |
| TCA | GCC | TCA | GCG | TGA | CCCCTGCTGC | | CAATCAATAA | | CGGCAGCGCG | | TTGTAGTGAT | | | | | 2032 |
| ser | ala | ser | ala | | | | | | | | | | | | | |
| | | 485 | | | | | | | | | | | | | | |
| GGAACCGGGC | | CTCTGTGGCC | | CGGTTTTTGT | | TTGCACTGGT | | CGGGCTTGTT | | AAAGGCTTGT | | | | | | 2092 |
| GCTTTCCATT | | TCCCCACTTA | | TACTGGCGCC | | ATCTTGTCGG | | AGTGCCAACC | | GTCGAACGAC | | | | | | 2152 |
| GCGAGGCTGA | | GACCGTTAAT | | TCGGGATCCG | | TGCAACCTCA | | TCAGGCTAGC | | ACCTGCGAAG | | | | | | 2212 |
| GGAAACAAGG | | GTAACTTGCG | | GGTTGCCGCG | | CCGGGGGAGG | | GACAAGCCTC | | TCCGCGTCAT | | | | | | 2272 |
| CAAGAGGAGC | | CATTCCTCGA | | TGAGTCAGGG | | CGCACAAGAG | | GGACTCTGTC | | CCGTCCGGTC | | | | | | 2332 |
| TGCCCAGGAG | | GGGC | | | | | | | | | | | | | | 2346 |

( 2 ) INFORMATION FOR SEQ ID NO:2:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( x i ) SEQUENCE DESCRIPTION: SEQ ID NO:2:

ATGCAAAAAA TAAAACTAAC TGGCTTG        27

( 2 ) INFORMATION FOR SEQ ID NO: 3:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( x i ) SEQUENCE DESCRIPTION: SEQ ID NO:3:

CGCTGAGGCT GACTTGAACG GAAGCCC        27